United States Patent [19]
Ricks

[11] Patent Number: 5,468,148
[45] Date of Patent: Nov. 21, 1995

[54] REMOTELY CONTROLLED DENTAL SYRINGE

[76] Inventor: Melvin D. Ricks, 245 Berkshire Ave., La Canada, Calif. 91011

[21] Appl. No.: 174,413

[22] Filed: Dec. 28, 1993

[51] Int. Cl.⁶ .......................... A61G 17/02; A61G 17/06
[52] U.S. Cl. ................. 433/80; 433/87; 433/91; 433/95
[58] Field of Search .................. 433/80, 82, 84, 433/85, 87, 88, 98, 99, 100

[56] References Cited

U.S. PATENT DOCUMENTS

| | | | |
|---|---|---|---|
| 3,971,375 | 7/1976 | Hill | 433/98 X |
| 4,276,023 | 6/1981 | Phillips et al. | 433/100 X |
| 4,299,221 | 11/1981 | Phillips et al. | 433/100 X |

Primary Examiner—Nicholas D. Lucchesi
Attorney, Agent, or Firm—J. E. Brunton

[57] ABSTRACT

A dental syringe for the controlled injection of air and water into a patient's mouth that effectively prevents the spread of contamination from patient to patient during the performance of dental procedures. The syringe comprises a one, piece, combination dispensing tip, head portion and handle portion that is constructed of plastic so that it can be disposed of after use. The air operated valves that control the flow of water and air through the dispensing tip are remotely located from the dispensing head so that they are not exposed to contamination during the performance of the dental procedure. The control valves of the apparatus can be easily operated by the thumb of the operator in a manner to effortlessly and precisely control the flow of air and water through the dispensing tip.

18 Claims, 3 Drawing Sheets

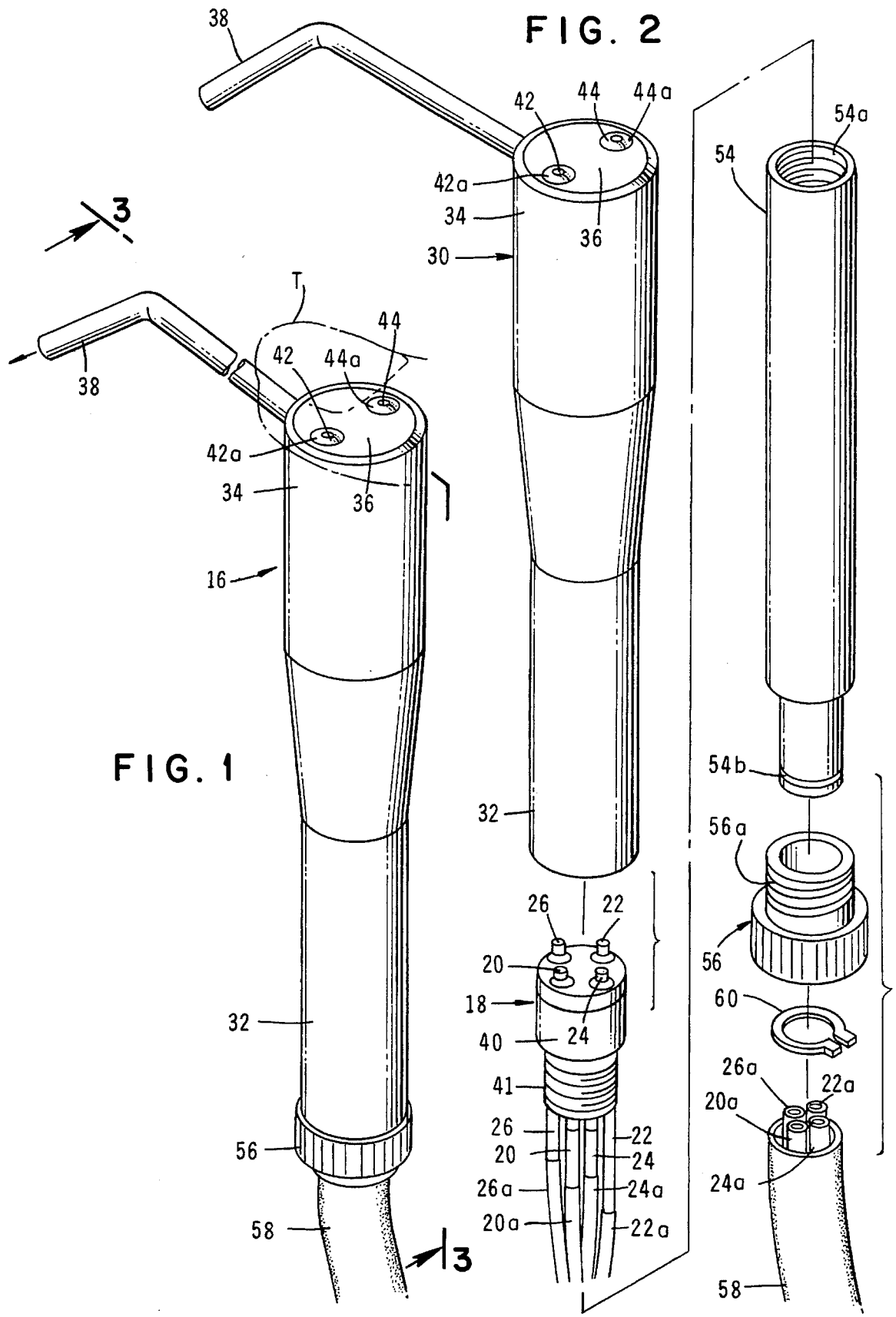

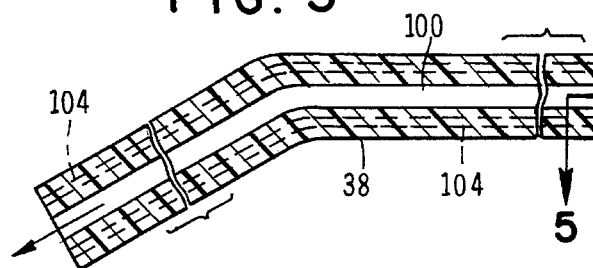
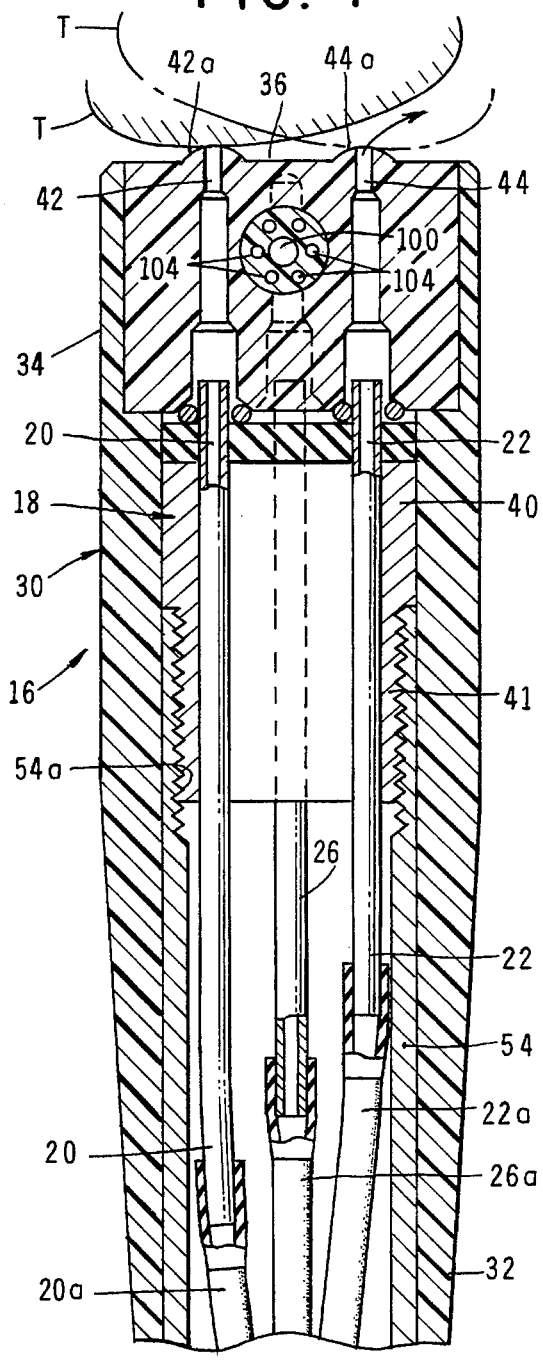
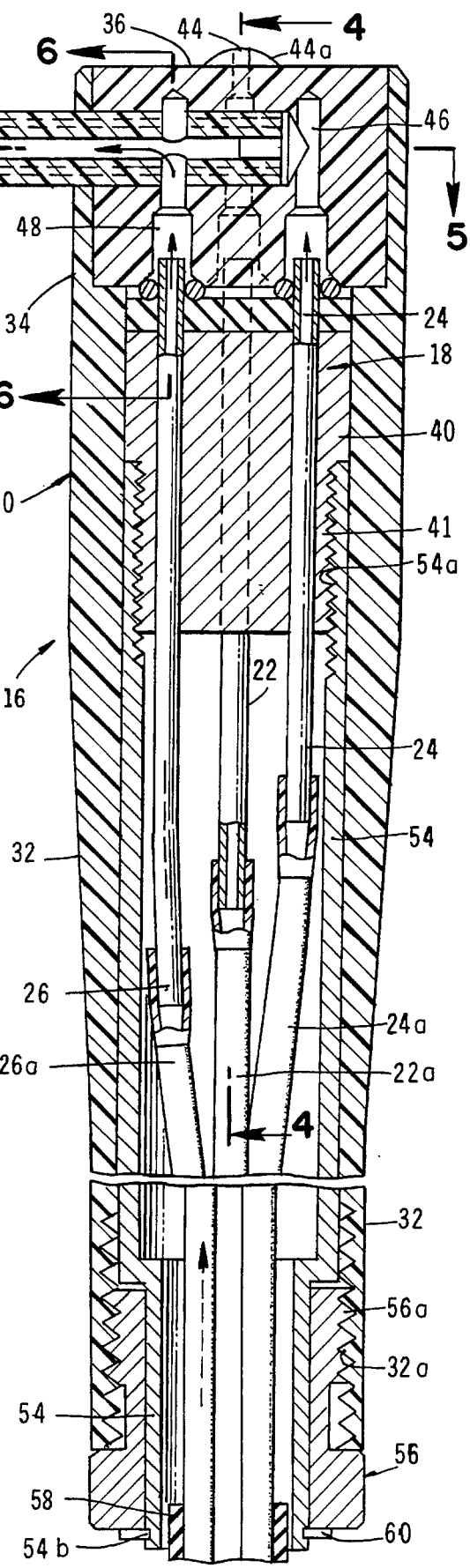

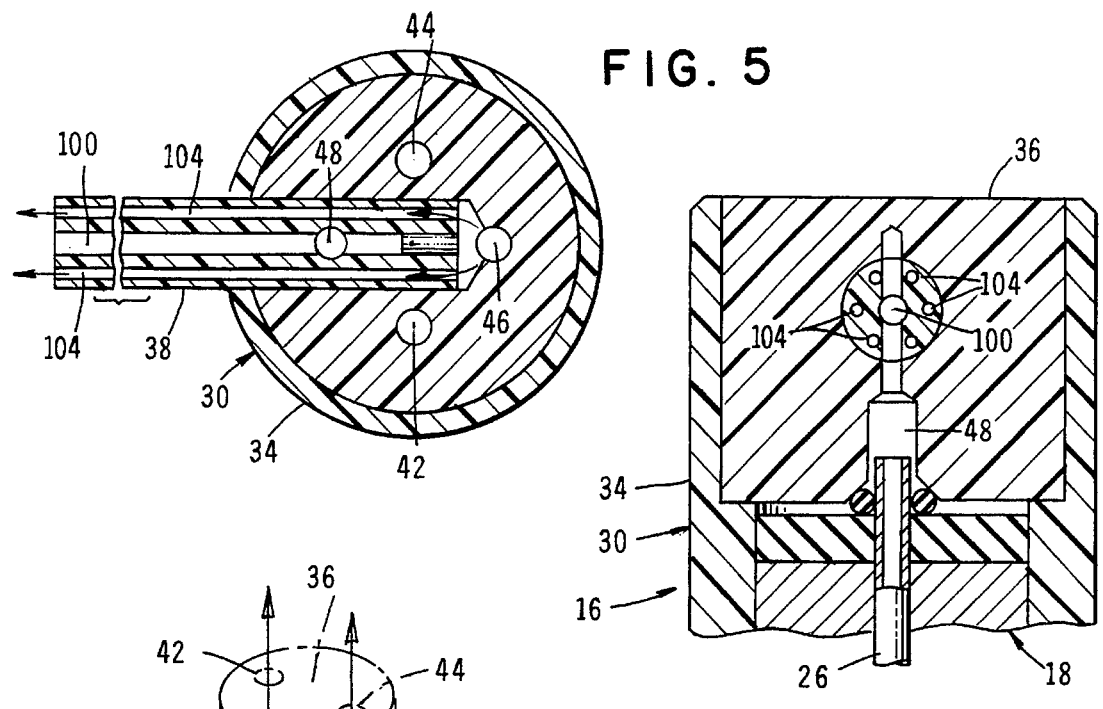
FIG. 5
FIG. 6
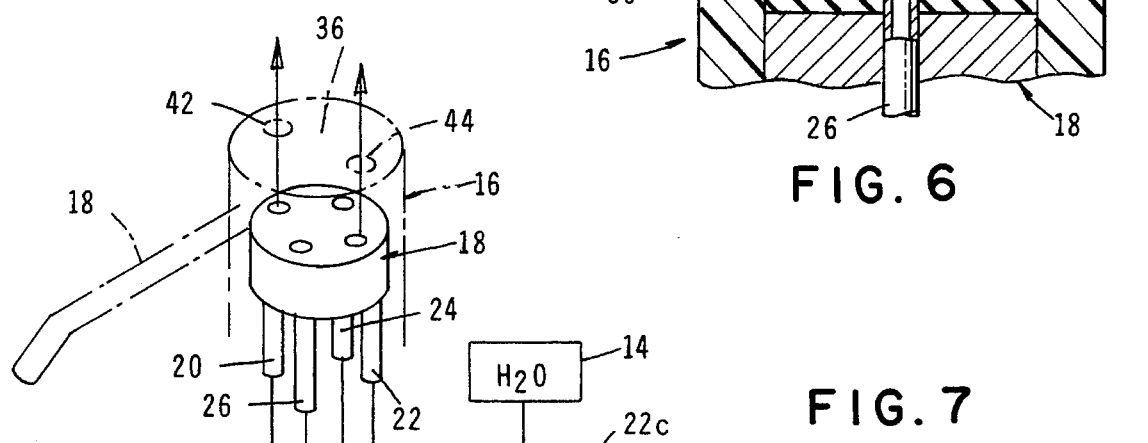
FIG. 7

REMOTELY CONTROLLED DENTAL SYRINGE

BACKGROUND OF THE INVENTION

1. Field of the Invention

The present invention relates generally to dental syringes for injecting air and water into a patient's mouth. More particularly, the invention concerns a dental syringe having a disposable dispensing head, the control valving for which is remotely located.

2. Discussion of the Invention

In order to prevent spread of contamination, it is necessary to either sterilize or dispose of tools and equipment that are used in or about a patient's mouth during the performance of dental procedures. By way of example, dental drills, picks mirrors, clamps and the like are normally sterilized after each use. On the other hand, swabs, packings and the like are, of course, disposed of in a sterile container after use.

Certain instruments such as dental syringes of the character which eject air and water in the patient's mouth present a more difficult problem. While it is possible to provide a hand-held dental syringe with a disposable, fluid-dispensing tip, the dispensing head itself is typically too expensive to discard and, because it houses the somewhat complex air and water-dispensing control valves, is virtually impossible to effectively sterilize.

As a general rule, the prior art dental syringe comprises a stainless steel head portion which includes an elongated, curved fluid dispensing tip that is threadably connected to the head. Integral with the head portion of the syringe is a handle portion which houses the fluid conduits that controllably supply air and water to the dispensing tip. The control valves which control the flow of air and water toward the dispensing tip are typically housed within the head portion of the syringe and comprise outwardly extending finger engaging valve operating elements which can be depressed by the dentist to regulate the flow of air and water out of the dispensing tip and into the patient's mouth. While in many such prior art devices the dispensing tip is formed of plastic and can be removed from the head and discarded, the head and handle portion, which also become contaminated, are much to expensive to discard after each use. Accordingly, the head and handle portion must be sterilized, to the extent possible, before treating the next patient. As previously mentioned, the somewhat complex and delicate control valves that are housed within the head portion or the instrument preclude high temperature sterilization and do not lend themselves to meaningful sterilization by chemical means.

SUMMARY OF THE INVENTION

It is an object of the present invention to provide a dental syringe of a special construction that effectively prevents the spread of contamination from patient to patient during the performance of dental procedures. More particularly, the dental syringe of the present invention comprises a one-piece, combination dispensing tip, head portion and handle portion that is constructed of plastic so that it can be disposed of after use.

It is another object of the invention to provide a dental syringe of the aforementioned character in which the valves that control the flow of water and air through the dispensing tip are remotely located from the dispensing head so that they are not exposed to contamination during the performance of the dental procedure.

Another object of the invention is to provide a dental syringe of the character described in the preceding paragraphs in which the control valves of the apparatus can be easily operated by the thumb of the operator in a manner to effortlessly and precisely control the flow of air and water through the dispensing tip. More particularly, the remotely located, air actuated valves, which control the flow of air and water, are operated by controllably restricting the flow of air through two small control air passageways that extend through the top of the head portion of the device.

Another object of the invention is to provide a dental syringe of unique construction in which the disposable dispensing head can be quickly and easily disconnected from the apparatus following the treatment of each patient. The disposable dispensing head is preferably formed from a rigid, light-weight, moldable plastic and is specially designed so that the air passageways that control the remotely located air and water valves protrude slightly above the upper wall of the syringe head for convenient access to the thumb and fingers of the operator.

Another object of the present invention is to provide a dental syringe of the class described in which the disposable dispensing head can be manufactured very inexpensively using well-known injection molding techniques.

BRIEF DESCRIPTION OF THE DRAWINGS

FIG. 1 is a generally perspective view of one form of the remotely controlled dental syringe of the present invention.

FIG. 2 is an exploded, generally perspective view of the dental syringe shown in FIG. 1.

FIG. 3 is an enlarged, cross-sectional view taken along lines 3—3 of FIG. 1.

FIG. 4 is a cross-sectional view taken along lines 4—4 of FIG. 3.

FIG. 5 is a cross-sectional view taken along lines 5—5 of FIG. 3.

FIG. 6 is a cross-sectional view taken along lines 6—6 of FIG. 3.

FIG. 7 is a generally schematic view illustrating the arrangement of the control valves of the apparatus which control fluid flow through the dispensing head of the dental syringe.

DESCRIPTION OF THE INVENTION

Referring to the drawings and particularly to FIGS. 1, 2 and 7, one embodiment of the syringe apparatus of the present invention is there illustrated. The apparatus, which is used in connection with the performance of dental procedures, comprises a source of air under pressure 12 (FIG. 7) which may be an air compressor or a house air outlet, a source of water under pressure 14, and a hand-held dispensing unit generally designated by the numeral 16 (FIG. 1). As best seen in FIGS. 2, 3, and 4, the dispensing unit comprises a first, or inner, portion 18 having first and second control air conduits 20 and 22, an air outlet conduit 24, and a water outlet conduit 26. Receivable over first portion 18 is a second, or outer disposable portion 30 which is preferably constructed from a moldable plastic. Second portion 30 includes an elongated handle portion 32, a head portion 34, having a top surface 36, and a dispensing tip 38 which is connected to and extends outwardly from head portion 34. Head portion 34 is provided with control air passageways 42 and 44, an air passageway 46 and a water passageway 48 (FIGS. 3 and 4).

In the embodiment of the invention shown in the drawings, first portion 18, which comprises a part of the connector means of the invention for connecting the remote sources of air and water to the dispensing unit, includes generally cylindrically shaped metal or plastic body 40 having an externally threaded, downwardly extending skirt portion 41. Control air conduits 20 and 22 carrying control air to passageways 42 and 44 of head portion 34, while conduits 24 and 26 carry air and water to passageways 46 and 48 respectively for controlled injection into the patient's mouth. Conduits 42 and 44 terminate in upstanding protuberances 42a and 44a which extend slightly above top wall 36 of outer portion 30 (FIGS. 1 and 2).

As best seen in FIG. 2, threaded skirt portion 41 of member 40 is threadably connected to threads 54a of an elongated internally threaded, tubular member 54 over which handle portion 32 is telescopically received. A connector ring 56, functions to interconnect second portion 30 and member 54. An elongated hollow tubular sheath 58, which also forms a part of the connector means, extends into member 54. Seath 58 surrounds elongated supply tubes 20a, 22a, 24a, and 26a, which are connected to the remotely located sources of air and water via valve means, the character of which will presently be described. As indicated in FIG. 2, tube 20a is connected at its upper end to conduit 20, while tube 22a is connected at its upper end to conduit 22 so as to supply air and water to the dispensing unit in a manner presently to be described.

As best seen in FIG. 3, connector member 56 is provided with external threads 56a which are threadably received within internal threads 32a provided in handle portion 32 so that member 54 will be securely retained within second portion 30. A split ring 60 is removably received within a groove 54b formed in member 54 (FIG. 2) and functions to hold member 54 in position relative to connector ring 56 (FIG. 3).

Referring now to FIG. 7, it can be seen that tubes 20a, 22a, 24a, and 26a, of the connector means are appropriately interconnected with first and second valve means which function to control the flow of air and water through the dispensing unit. As shown in the lower portion of FIG. 7, a conduit 63 interconnects air source 12 with an air regulator 64 which forms a part of the valve means. Connected in series with air regulator 64 are chokes 66 and 68, the purpose of which will presently be described. Air regulator 64 can be any type of commercially available, miniature air regulator, but is preferably a self-relieving, piston-type, adjustable air regulator of the character commercially available from the Clippard Company and sold by that company under the designation "MAR-1". An adjustment knob 64a permits micro-adjustment of the regulator both upwardly and downwardly to provide regulated output pressures of up to 100 pounds per square inch gauge (psig) maximum. Chokes 66 and 68, of the character also readily commercially available from the Clippard Company under the designation "MAC", have proven quite satisfactory. Chokes 66 and 68 preferably comprise in-line, fixed orifice air chokes, which can be calibrated for precise flow rates therethrough. As indicated in FIG. 7, choke 66 is interconnected with tubing 20a by means of a conduit 70 and a tee 73, while choke 68 is interconnected with tube 22a by means of a conduit 72 and a tee 75. With this arrangement, a precisely regulated air stream can be derived from air source 12 and caused to continuously flow through control air passageways 42 and 44 of dispenser portion 30. Air flowing from choke 66 through conduit 70 also flows to the first valve means of the invention via tee 73 and a conduit 74. Similarly, air flowing from choke 68 flows to the second valve means of the invention via tee 75 and conduit 78.

As indicated in FIG. 7, the first valve means of the present embodiment of the invention, comprises an assemblage made up of a control valve 82 and an air pilot actuator 84. Control valve 82 has an inlet port 82a which, as shown in FIG. 7, is interconnected with air source 12 by means of a conduit 88. Control valve 82 also has an outlet port 82b which is connected to tube 24a. In the manner presently to be described, the first valve means functions to control the flow of air through tube 24a in response to operator restriction of control air flowing through control air passageway 42. Control valve 82 can be any type of commercially available, miniature control valve, but, once again, a valve manufactured and sold by Clippard Company under the designation "MAV-3" has proven quite satisfactory. This valve is a normally closed, three-way poppet valve having a working range of 300 psig maximum. The valve, in operation, increases pressure proportionally as the plunger of the valve is depressed as a result of restriction of the control air flowing through outlet 42. When the plunger is released, the output port is exhausted to atmosphere and the input port is closed. Further details of operation and construction of the "MAV-3" control valve is readily available from the Clippard Company.

Air pilot actuator 84 can also be any type of readily commercially available pilot actuator for actuating the flow control valve 82. However, as before, a valve manufactured and sold by the Clippard Company under the designation "MPA-7" has proven satisfactory for the purpose. This pilot actuator comprises a single-acting, spring-return, miniature pilot actuator having an input pressure of 250 psig maximum.

The second valve means of the apparatus of the present form of the invention for controlling the flow of water through the water outlet of the dispenser head, comprises an assembly made up of a water-flow control valve 90 and an air pilot actuator 92 FIG. 7). Valve 90 is also available from the Clippard Company under the designation "MAR-1C". This valve comprises a normally closed, three-way piston-type valve with variable pressure output. In operation, the valve increases pressure proportionately as the plunger is depressed as a result of restriction of the control air flowing through outlet 44. When the plunger is released, the output port is exhausted to atmosphere and the input port is closed. Pilot actuator 92 is of the same general character as pilot actuator 84 and a Clippard Company actuator sold under the designation "MPA-7" has proven satisfactory for use as a part of the second valve means of the invention.

As shown in FIG. 7, water flow control valve 90 has an inlet port 90a which is interconnected with water source 14 by means of a conduit 94. Flow control valve 90 also has an outlet port 90b which is interconnected with tube 26a in the manner shown in FIG. 7.

Turning now to FIGS. 3, 4, 5 and 6, it is to be observed that water passageway 48 is in communication with a central water flow passageway 100 provided in dispensing tip 38 while air passageway 46 is in communication with a plurality of circumferentially spaced air flow passageways 104 provided in dispensing tip 38 (FIG. 3).

Operation

With the apparatus of the invention interconnected in the manner shown in FIGS. 1 and 7, the operator grasps the handle portion 32 of the dispensing unit and positions the thumb "T" over one or both of the control air passageways 42 and 44. As previously mentioned a stream of control air is continuously flowing from air source 12 through passageway 42 from via conduit 63, air regulator 64, choke 66, passageway 70, conduit 20a, and conduit 20 (FIG. 7). If control air passageway 42 is blocked, by the operator, it is apparent that a pressure build-up will result within air pilot actuator 84. This build-up of air pressure will cause normally closed control valve 82 to open thereby permitting air to flow from the outlet of the control valve 82b through tubing 24a, conduit 24, passageway 46 and then outwardly through circumferentially spaced air passageways 104 provided in dispenser tip 38. The more firmly the operator presses his thumb over the control air passageway, the greater will be the pressure build-up within the pilot actuators and the greater will be the rate of flow of air and water through the valve means.

Control air is also continuously flowing through control air passageway 44 from air source 12 via passageway 63, regulator 64, choke 58, passageway 72, tubing 22a and conduit 22. When the operator using a thumb or forefinger restricts free flow of control air outwardly of passageway 44, a pressure build-up will result within pilot actuator 92 of water flow control valve 90. This build-up in pressure within pilot actuator 92 causes the normally closed water flow control valve 90 to open. With the valve in an open position, water is permitted to flow from outlet port 90b through tubing 26a and conduit 26. Water flowing through conduit 26 will then flow through centrally disposed passageway 100 provided in dispenser tip 38 and outwardly into the patient's mouth. As previously mention, water is supplied to water flow control valve 90 from the water source 14 via conduit 94.

When the operator restricts free air flow through both control air passageways 42 and 44, an air pressure build-up will result in both air pilot actuators 84 and 92 causing both valves 82 and 90 to open thereby causing the simultaneous flow of air and water outwardly of air passageways 104 and water passageway 100 of the dispenser tip 38.

The flow of control air through passageways 42 and 44 can be precisely regulated by air regulator 64 and chokes 66 and 68. When the control air flow is thus precisely regulated, extremely fine adjustments can be made of the water and air flowing outwardly of the dispensing tip 38 by either partial or complete closure of control air passageways 42 and 44 by the thumb or fingers of the operator. In this way, precise flow of air, precise flow of water, or precise flow of a mixture of air and water can be easily and effortlessly accomplished by the operator applying varying closure pressures on control air passageways outlets 42 and 44.

After the treatment of the particular patient has been completed, split ring 66 is removed from the assemblage and connector ring 56 is threadably removed from outer portion 30. Outer porter 30 can then be freely slipped over portions 40 and 54 and discarded. A new, sterile outer dispenser unit portion can then be inserted over members 40 and 54 and connector ring 56 can once again be threadably connected to the lower extremity of outer portion 30. After split ring 60 is repositioned within groove 54b, the apparatus is once again ready for use in treating the next patient.

It is to be understood that various commercially availably air regulators, pilot actuators and contact valves can be used to construct the valve means of the apparatus. Such devices are well understood by those skilled in the art and can easily be assembled together to perform the desired function.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dental syringe for controllably directing a flow of air and water into a patient's mouth from a remote source of air and water, said dental syringe comprising:
   (a) a hand-held dispensing unit including:
      (i) dispensing means for dispensing air and water, said dispensing means including a handle comprising a generally cylindrically shaped body portion having an axial center line and including an upper end portion, said handle further including a head portion disposed proximate said upper end portion, said head portion having a top surface extending generally perpendicular to said axial center line and being provided with first and second apertures, said dispensing means further including a dispensing tip connected to said head portion, and having an air outlet, a water outlet, and first and second control air passageways in communication with said first and second apertures; and
      (ii) connector means associated with said dispensing means for interconnecting said air outlet and said water outlet thereof with the remote sources of air and water respectively, and for connecting said first and second control air passageways with the remote source of air;
   (b) first valve means associated with said connector means for controlling the flow of air through said air outlet of said dispensing means in response to at least a partial closure of said first aperture to cause a restriction of the flow of air through said first control air passageway of said dispensing means; and
   (c) second valve means associated with said connector means for controlling the flow of water through said water outlet of said dispensing means in response to at least a partial closure of said second aperture to cause a restriction of the flow of air through said second control air passageway of said dispensing means.

2. A dental syringe as defined in claim 1 in which said dispensing means comprises a dispensing tip having air and water passageways therethrough adapted to be connected to said remote sources of air and water via said first and second valve means.

3. A dental syringe for controllably directing a flow of air and water into a patient's mouth from a remote source of air and water, said dental syringe comprising:
   (a) a hand-held dispensing unit including:
      (i) a disposable outer portion for dispensing air and water, said outer portion having an air outlet, a water outlet, and first and second control air passageways;
      (ii) in inner portion associated with said outer portion, said inner portion having:
         a. a supply air inlet and a supply air outlet connected to said air outlet of said outer portion;
         b. a supply water inlet and a supply water outlet connected to said water outlet of said outer portion; and
         c. first and second control air inlets and first and second control air outlets connected to said first and second control air passageways of said outer portion;

(b) a first remotely located, air operated valve connected to said supply air inlet of said inner portion of said dispensing unit for controlling the flow of air through said air outlet in response to a restriction of the flow of air through said first control air passageway of said outer portion; and (c) a second remotely located, air operated valve connected to said supply water inlet of said inner portion of said dispensing unit for controlling the flow of water through said water outlet in response to a restriction of the flow of air through said second control air passageway of said outer portion.

4. An apparatus as defined in claim 3 in which said disposable outer portion is formed of moldable plastic.

5. An apparatus as defined in claim 3 in which said inner portion includes a generally cylindrically shaped metal body and an elongated tubular member connected to said metal body, said body and said tubular member being receivable within said outer portion.

6. An apparatus as defined in claim 3, further including an air regulator disposed intermediate said first and second valves and said source of air under pressure.

7. An apparatus as defined in claim 6 further including first and second chokes connected to said air regulator.

8. A syringe apparatus for use in performing dental procedures on a patient, comprising:
 (a) a source of air under pressure;
 (b) a source of water under pressure;
 (c) a hand-held dispensing unit comprising:
  (i) a first portion having first and second control air passageways, an air outlet passageway and a water outlet passageway, said first portion further comprising:
   a. an elongated handle portion;
   b. a hand portion having a top surface; and
   c. a dispensing tip having a central water flow passageway and a plurality of circumferentially spaced air flow passageways.
  (ii) a second portion connected to said first portion and including means for supplying air from said source of air under pressure to said first and second control air passageways and to said air outlet passageway of said first portion and means for supplying water from said source of water under pressure to said water outlet of said first portion;
 (d) first valve means connected to said second portion of said dispensing unit, said first valve means being operable by restricting the flow of air through said first control air passageway of said first portion for controlling the flow of water through said water outlet of said first portion; and
 (e) second valve means connected to said second portion of said dispensing unit, said second valve means being operable by restricting the flow of air through said second control air passageway of said first portion for controlling the flow of air through said air outlet of said first portion.

9. An apparatus as defined in claim 8 in which said first and second air control passageways extend through said head portion and terminate in upstanding protuberances formed on said top surface.

10. An apparatus as defined in claim 8 in which said second portion comprises:
 (a) a generally cylindrically shaped body having an externally threaded skirt portion; and
 (b) an elongated generally tubular shaped member threadably connected to said body, said tubular shaped member being closely receivable within said elongated handle portion of said first portion of said dispensing unit.

11. An apparatus as defined in claim 10 in which said second portion further includes:
 (a) an elongated water supply tube having first and second ends, said first end being connected to said water outlet passageway of said first portion and said second end being connected to said first valve means; and
 (b) an elongated air supply tube having first and second ends, said first end being connected to said air outlet passageway of said first portion and said second end being connected to said second valve means.

12. An apparatus as defined in claim 11 in which both said water supply tube and said air supply tube are receivable within said tubular shaped member of said second portion and in which said second portion further includes:
 (a) a first control air supply tube having first and second ends, said first end being connected to said first control air passageway and said second end being connected to said first valve means; and
 (b) a second control air supply tube having first and second ends, said first end being connected to said second control air passageway and said second end being connected to said second valve means.

13. A syringe apparatus for use in performing dental procedures on a patient, comprising:
 (a) a source of air under pressure;
 (b) a source of water under pressure;
 (c) a dispensing unit comprising:
  (i) a first portion having first and second control air passageways, an air outlet passageway and a water outlet passageway, said first portion further comprising:
   a. a handle having a top surface;
   b. a dispensing tip connected to said handle, said dispensing tip having a water outlet connected to said water outlet passageway of said first portion and at least one air outlet connected to said air outlet passageway of said first portion;
  (ii) a second portion connected to said first portion and including means for supplying air from said source of air under pressure to said first and second control air passageways and to said air outlet passageway of said first portion and means for supplying water from said source of water under pressure to said water outlet of said first portion;
 (d) first valve means connected to said second portion of said dispensing unit, said first valve means being operable by restricting the flow of air through said first control air passageway of said first portion for controlling the flow of water through said water outlet of said first portion; and
 (e) second valve means connected to said second portion of said dispensing unit, said second valve means being operable by restricting the flow of air through said second control air passageway of said first portion for controlling the flow of air through said air outlet of said first portion.

14. An apparatus as defined in claim 13 in which said first and second air control passageways extend through said top surface of said handle and terminate in closable apertures.

15. A dental syringe for controllably directing a flow of air and water into a patient's mouth from a remote source of air and water, said dental syringe comprising:

(a) a dispensing unit including:
   (i) an outer portion for dispensing air and water, said outer portion having an air outlet, a water outlet, and first and second control air passageways;
   (ii) an inner portion associated with said outer portion, said inner portion having:
      a. a supply air inlet and a supply air outlet connected to said air outlet of said outer portion;
      b. a supply water inlet and a supply water outlet connected to said water outlet of said outer portion; and
      c. first and second control air inlets and first and second control air outlets connected to said first and second control air passageways of said outer portion;

(b) a first remotely located valve means connected to said supply air inlet of said inner portion of said dispensing unit for controlling the flow of air through said air outlet in response to a restriction of the flow of air through said first control air passageway of said outer portion; and (c) a second remotely located, valve means connected to said supply water inlet of said inner portion of said dispensing unit for controlling the flow of water through said water outlet in response to a restriction of the flow of air through said second control air passageway of said outer portion.

16. A dental syringe for controllably directing a flow of air and water into a patient's mouth from a remote source of air and water, said dental syringe comprising:

(a) a hand-held dispensing unit including:
   (i) dispensing means for dispensing air and water, said dispensing means including a dispensing tip connected to a handle having a top surface provided with first and second apertures and having an air outlet, a water outlet, and first and second control air passageways in communication with said first and second apertures; and
   (ii) connector means associated with said dispensing means for interconnecting said air outlet and said water outlet thereof with the remote sources of air and water respectively, and for connecting said first and second control air passageways with the remote source of air, said connector means comprising a body receivable within said handle, said body having first and second control air conduits connected to said first and second control air passageways of said dispensing means, a water conduit connected to said water passageway of said dispensing means and an air conduit connected to said air passageway of said dispensing means;

(b) first valve means associated with said connector means for controlling the flow of air through said air outlet of said dispensing means in response to at least a partial closure of said first aperture to cause a restriction of the flow of air through said first control air passageway of said dispensing means; and (c) second valve means associated with said connector means for controlling the flow of water through said water outlet of said dispensing means in response to at least a partial closure of said second aperture to cause a restriction of the flow of air through said second control air passageway of said dispensing means.

17. A dental syringe as defined in claim 16 in which said first and second valve means comprise first and second air operated valves respectively, said first and second air operated valves being connected to said first and second control air conduits of said connector means respectively.

18. A dental syringe as defined in claim 17 in which one of said first and second air operated valves is connected to said water conduit of said connector means and the other of said first and second air operated valves is connected to said air conduit of said connector means.

* * * * *